United States Patent [19]
Newell et al.

[11] Patent Number: 5,694,210
[45] Date of Patent: Dec. 2, 1997

[54] MULTI-PURPOSE SENSOR SYSTEM AND SENSING METHOD USING INTERNALLY REFLECTED LIGHT BEAMS

[75] Inventors: Ty A. Newell, Urbana; Evan Hurlburt, Champaign, both of Ill.

[73] Assignee: The Board of Trustees of the University of Illinois, Urbana, Ill.

[21] Appl. No.: 673,299

[22] Filed: Jun. 28, 1996

[51] Int. Cl.$^6$ ............ G01N 21/41; G01B 11/06; G01P 3/36
[52] U.S. Cl. ............ 356/128; 356/381; 356/382; 356/28
[58] Field of Search ............ 356/381, 382, 356/27, 28, 128, 337, 338, 70, 136

[56] References Cited

U.S. PATENT DOCUMENTS

| | | |
|---|---|---|
| 4,039,845 | 8/1977 | Oberhansli et al. |
| 4,201,467 | 5/1980 | Hartmann et al. .......... 356/28 |
| 4,240,751 | 12/1980 | Linnecke et al. |
| 4,320,291 | 3/1982 | Uramoto |
| 4,687,925 | 8/1987 | Huggins et al. .......... 356/28 |
| 4,713,552 | 12/1987 | Denis et al. |
| 4,804,268 | 2/1989 | Mohnsen et al. .......... 356/28 |
| 4,909,588 | 3/1990 | Harner et al. |
| 4,984,894 | 1/1991 | Kondo .......... 356/382 |
| 4,998,022 | 3/1991 | Tregay |
| 5,396,079 | 3/1995 | Evers et al. |

OTHER PUBLICATIONS

A. Bayani et al., Online Measurement of Oil Concentrations of R–134a/Oil Mixtures with a Density Flowmeter, HVAC&R Research, p. 232–241 (Jul. 1995).

J.J. Baustian et al., Properties of Oil–Refrigerant Liquid Mixtures with Applications to Oil Concentration Measurement: Part I—Thermophysical and Transport Properties, ASHRAE Transactions, pp. 55–73 (1986), no month available.

J.J. Meyer et al., An Ultrasonic Device for Measuring the Oil Concentration in Flowing Liquid Refrigerant, Int'l J. Refrigeration, pp. 481–486 (1994), no month available.

S. Suzuki et al., Measuring Method of Oil Circulation Ratio Using Light Absorption, ASHRAE Transactions, pp. 413–421, no date unavailable.

K. Kutsuna et al., Real Time Oil Concentration Measurement in Automotive Air Conditioning by Ultraviolet Light Absorption, SAE Technical Paper Series No. 910222, pp. 1–8, (Feb.–Mar. 1991).

D. T. Bostick et al., Real–Time In–Situ Refractometer For concentration Mesurements In Absorption Machines, pp. 174–186, no date available.

L.W. Evers et al., Liquid Film Thickness Measurements By Means Of Internally Reflected Light, SAE Technical Paper Series No. 950002 (Feb.–Mar. 1995), pp. 1–7.

*Primary Examiner*—Frank G. Font
*Assistant Examiner*—Amanda Merlino
*Attorney, Agent, or Firm*—Wood, Phillips, VanSanten, Clark & Mortimer

[57] ABSTRACT

A sensor system including a first layer having first and second surfaces and a first index of refraction, a second layer having a second index of refraction which is less than the first index of refraction, a mechanism for generating a first diffuse light beam which passes through the first layer from the first surface to the second surface, and a mechanism for sensing a portion of the first diffuse light beam reflected back through the first layer to the first surface as an incident of the first diffuse light beam impinging upon the second layer. Also a method of determining the properties of a medium, the method including the steps of generating a first diffuse light beam, passing the first diffuse light beam through a first surface of a first medium having a first index of refraction, causing a portion of the first diffuse light beam to pass through the first medium, to impinge upon a second medium having a second index of refraction less than the first index of refraction and to reflect back to the first surface, and sensing the portion of the first diffuse light beam reflected back to the first surface.

13 Claims, 3 Drawing Sheets

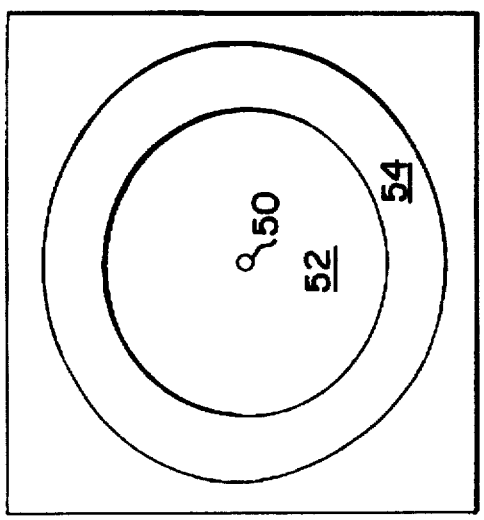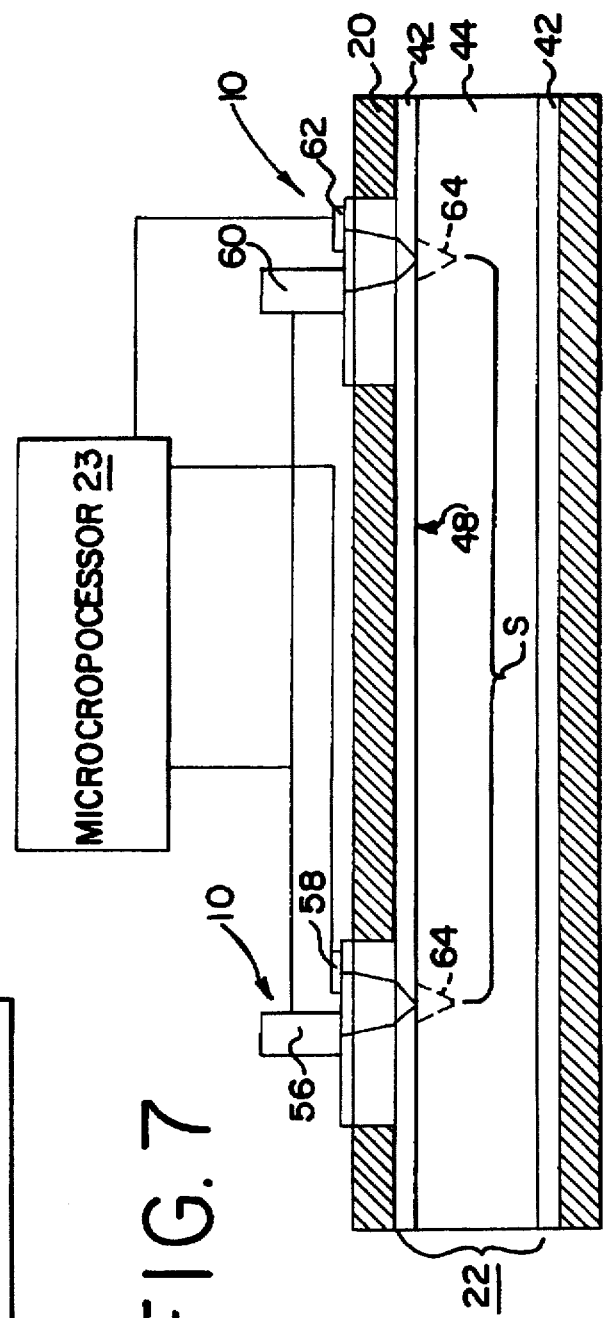

MULTI-PURPOSE SENSOR SYSTEM AND SENSING METHOD USING INTERNALLY REFLECTED LIGHT BEAMS

FIELD OF THE INVENTION

This invention is directed to a multi-purpose sensor system and sensing method, and in particular to a sensor system and sensing method that use a beam of diffuse light which is partially reflected at the interface between the sensor and a target medium, or at the interface between two target media, to sense different properties of the target medium or media.

BACKGROUND OF THE INVENTION

Many common industrial and commercial processes use a working fluid flowing from one location to another location within a system to achieve a desired result. For example, in the standard refrigeration cycle, the working fluid, commonly a mixture of a refrigerant and a small amount of a lubricant, such as oil, circulates in a closed loop between an evaporator and a condenser to lower the temperature of the environment adjacent to the evaporator relative to the environment adjacent the condenser.

For a number of different reasons, it may be desirable to measure the different properties of the working fluid, such as the density or the concentration of constituent fluids, in real time as the working fluid flows within the system. Real time measurements of the properties of the working fluid may then be integrated into the control of the system, to increase the responsiveness, and thereby the efficiency, of the system to changes in the working fluid. Additionally, accurate measurements of the changes in the properties of the working fluid may suggest a schedule for preventive maintenance, increasing the efficiency of the system by limiting downtime caused by repairs. In the air conditioning and refrigeration industry, measurement of the characteristics of the mixture of refrigerant and lubricant as the mixture circulates through the refrigeration system may assist in the selection of new, environmentally-friendly refrigerants to replace the standard refrigerants presently in use.

At the present time, few methods or devices exist which can be used to measure the properties of a working fluid both accurately and continuously in real time, while being sufficiently robust and inexpensive to permit widespread use. For example, the generally-accepted ASHRAE method for measuring the concentrations of refrigerant and oil in the working fluid in a refrigeration system is not well suited for use in real time data gathering. The ASHRAE method involves withdrawing and weighing multiple samples of the working fluid, boiling the refrigerant in the sample away slowly, weighing the remaining oil mass and then comparing the initial weight of the sample to the weight of the oil mass to determine the concentration of oil in the working fluid.

Several alternative methods have been suggested for use in the continuous, real time measurement of the concentration of oil in the working fluid of a refrigeration system. One suggestion has been to use density flowmeters to conduct the on-line measurement of oil concentrations in refrigerant/oil mixtures. A. Bayani et al., Online Measurement of Oil Concentrations of R-134a/Oil Mixtures with a Density Flowmeter, HVAC&R Research, pp. 232–241 (July 1995); J. J. Baustian et al., Properties of Oil-Refrigerant Liquid Mixtures with Applications to Oil Concentration Measurement: Part I—Thermophysical and Transport Properties, ASHRAE Transactions, pp. 55–73 (1986). A second suggestion has been to use ultrasound and correlate the acoustical velocity within the working fluid with the concentration of oil within the fluid. J. J. Meyer et al., An Ultrasonic Device for Measuring the Oil Concentration in Flowing Liquid Refrigerant, Int'l J. Refrigeration, pp. 481–486 (1994). A third suggestions has been to use the absorption characteristics of the working fluid to determine the concentration of oil in the working fluid. S. Suzuki et al., Measuring Method of Oil Circulation Ratio Using Light Absorption, ASHRAE Transactions, pp. 413–421; K. Kutsuna et al., Real Time Oil Concentration Measurement in Automotive Air Conditioning by Ultraviolet Light Absorption, SAE Technical Paper Series No. 910222 (Feb.–Mar. 1991).

A still further alternative method that has been suggested focuses on use of the refractive properties of the working fluid to measure the concentration of the oil in the fluid. One such method involves passing a beam of light rays along the interface between the working fluid and one of the inclined faces of a prism. As an incident of this method, areas of light and dark are generated on the opposite face of the prism so that the critical angle may be measured thereby and the index of refraction may be calculated therefrom. The data on the refractive index can then be correlated with the indices of refraction for various concentrations of oil in the refrigerant to determine the concentration of oil in the system.

Another refractive method was outlined by D. T. Bostick et al. in Real-Time In-Situ Refractometer for Concentration Measurements in Absorption Machines, wherein it was suggested that the concentration of oil in the working fluid may be correlated to the light loss from an optical fiber cable which has had a portion of the cladding removed therefrom as an incident of the immersion of the cable in a stream of the working fluid. It is suggested by Bostick et al. that the light lost is related to the critical angle at the fiber/fluid interface, which causes some light beams to be reflected within the cable and transmitted along the length of the cable, while causing other light beams to pass into the fluid and to become lost.

All of these alternative methods may have their drawbacks. Some of these methods may lack the robustness to withstand the wide variations which exist in pressure and temperature within the refrigeration system. Other methods may be too expensive or too cumbersome for widespread application in combination with real time control, maintenance and research systems.

SUMMARY OF THE INVENTION

In one aspect of the invention, a sensor system includes a first layer having first and second surfaces and a first index of refraction, a second layer having a second index of refraction which is less than the first index of refraction, a mechanism for generating a first diffuse light beam which passes through the first layer from the first surface to the second surface, and a mechanism for sensing a portion of the first diffuse light beam reflected back through the first layer to the first surface as an incident of the first diffuse light beam impinging upon the second layer. Moreover, the second layer may be disposed on the first layer so as to define an interface between the first and second layers, the portion of the first diffuse light beam reflected through the first layer to the first surface as an incident of the first diffuse light beam impinging the interface. Moreover, the sensor system may include a mechanism coupled to the sensing mechanism for determining the index of refraction of the second layer as a function of the distance along the first surface between the first diffuse light beam and the reflected portion of the first diffuse beam.

The sensor system may also include a third layer disposed between the first layer and the second layer having a thickness and a third index of refraction which is less than the first index of refraction and greater than the second index of refraction. Moreover, the second layer may be disposed on the third layer so as to define an interface between the second and third layers, the portion of the first diffuse light beam reflected through the first layer to the first surface as an incident of the first diffuse light beam impinging the interface. Moreover, the sensor system may include a mechanism coupled to the sensing mechanism for determining the thickness of the third layer as a function of the distance along the first surface between the first diffuse light beam and the reflected portion of the first diffuse beam.

The sensor system may be combined with a mechanism for generating a second diffuse light beam which passes through the first layer from the first surface to the second surface, the second diffuse light beam generating mechanism disposed a predetermined distance from the first diffuse light beam generating mechanism, a mechanism for sensing a portion of the second diffuse light beam reflected back through the first layer to the first surface as an incident of the second diffuse light beam impinging the interface defined between the second and third layers, and a mechanism coupled to the first and second diffuse light beam sensing mechanisms for determining the velocity of a localized disturbance in the thickness of the third layer as a function of the time elapsed between the first and second diffuse light beam sensing mechanisms sensing the portions of the first and second light beams reflected through the first layer as an incident of a change in thickness of the third medium caused by the localized disturbance.

In another aspect of the invention, a method of determining the properties of a medium includes the steps of generating a first diffuse light beam, passing the first diffuse light beam through a first surface of a first medium having a first index of refraction, causing a portion of the first diffuse light beam to pass through the first medium, to impinge upon a second medium having a second index of refraction less than the first index of refraction and to reflect back to the first surface, and sensing the portion of the first diffuse light beam reflected back to the first surface. Moreover, the causing step may include causing the portion of the first diffuse light beam to impinge an interface defined between the first and second media and reflect back to the first surface. Moreover, the method may include the steps of measuring the distance along the first surface between the first diffuse light beam and the portion of the first diffuse light beam reflected back to the first surface, and determining the index of refraction of the second medium as a function of the distance along the first surface between the first diffuse light beam and the portion of the first diffuse light beam reflected back to the first surface.

The causing step may include causing the portion of the first diffuse light beam to pass through a third medium having a thickness and a third index of refraction which is less than the first index of refraction and greater than the second index of refraction, the third medium disposed between the first and second media, and causing the portion of the first diffuse light beam to impinge an interface defined between the second and third media and to reflect back to the first surface. Moreover, the method may include the steps of measuring the distance along the first surface between the first diffuse light beam and the portion of the first diffuse light beam reflected back to the first surface, and calculating the thickness of the third medium as a function of the distance along the first surface between the first diffuse light beam and the portion of the first diffuse light beam reflected back to the first surface.

The method may include sensing a portion of the first diffuse light beam reflected back to the first surface as an incident of a disturbance moving along the interface between the second and third media, generating a second diffuse light beam, passing the second diffuse light beam through the first surface of the first medium at a predetermined distance from the first diffuse light beam, sensing a portion of the second diffuse light beam reflected back to the first surface as an incident of the disturbance moving along the interface between the second and third media, measuring the time elapsed between the step of sensing of the portion of the first diffuse light beam reflected back as an incident of the disturbance moving along the interface between the second and third media and the step of sensing the portion of the second diffuse light beam reflected back as an incident of the disturbance moving along the interface between the second and third media, and determining the velocity of the disturbance moving along the interface between the second and third media as a function of the time elapsed between the step of sensing the portion of the first diffuse light beam reflected back to the first surface as an incident of the disturbance moving along the interface between the second and third media, and the step of sensing the portion of the second diffuse light beam reflected back to the first surface as an incident of the disturbance moving along the interface between the second and third media.

BRIEF DESCRIPTION OF THE DRAWINGS

FIG. 6 is a plan view of a first or upper surface of a transparent layer or sight glass of the sensor of FIG. 5 showing the different regions of shadow and light produced during operation of the sensor; and FIG. 7 is a partial cross-sectional schematic view of a system on a passage or conduit using a plurality of sensors according to an embodiment of the present invention configured so as to sense the velocity of a wave propagating along the interface of a liquid phase and a vapor phase in a two-phase fluid system.

DESCRIPTION OF THE PREFERRED EMBODIMENTS

The present invention utilizes the internal reflection occurring at the interface between media having different indices of refraction to measure different properties of a fluid flowing past an embodiment of the present invention. In particular, a beam of diffuse light with a plurality of light rays is passed through a first medium having a first index of refraction. As the individual rays of the diffuse light beam impinge on the interface between the first medium and a second medium having a second index of refraction, the second index being less than the first index, a first set of light rays will be reflected back through the first medium, while a second set of light rays are passed into the second medium. By measuring the distance from the center of the light beam to the innermost light ray reflected back through the medium, the index of refraction of the second medium may be calculated using the geometry of the sensor and Snell's law. The rapid transition to total internal reflection allows for a high degree of precision and measurability to be achieved.

Extending this basic principle a step further, if a third medium having a third index of refraction is disposed in series with the second medium, then a second separation of the light rays originally generated as part of the diffuse light beam will occur at the interface between the second and third media. As a consequence, a first subset of the second set of light rays will be reflected back through the first and second media. By measuring the distance between the center of the light beam and the innermost light ray reflected through the first and second media, the thickness of the second medium may be calculated from the geometry of the multi-media system and Snell's law.

Given the ability of the sensor to measure the thickness of the second medium, it is also possible for the sensor to measure changes at the interface between the second and third media which result in a change in the thickness of the second medium. For example, using a pair of sensors fabricated according to an embodiment of the present invention, the velocity of propagation of a wave moving along the interface between the second and third media may be calculated by placing the sensors at two locations, one downstream from the other, and timing the reactions of the two sensors to a localized disturbance in thickness of the second media caused by the wave as it propagates.

Figure 1:
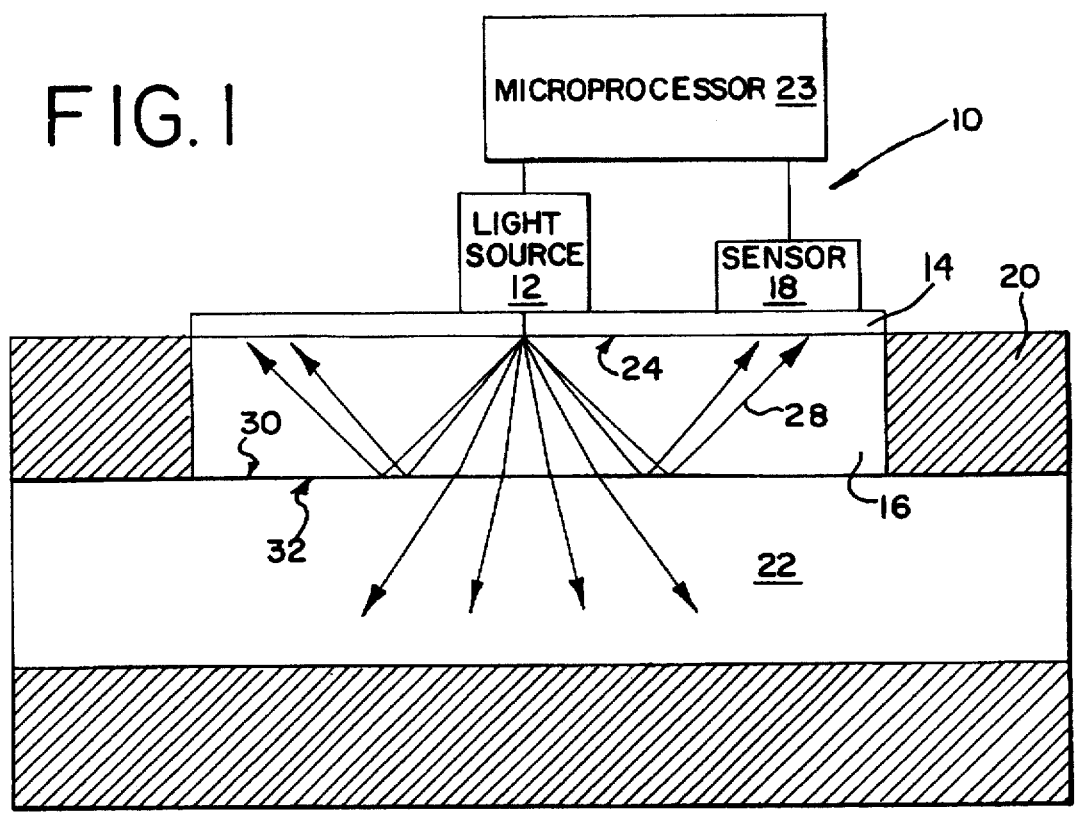
FIG. 1 is a partial cross-sectional schematic view of an embodiment of a sensor according to the present invention on a passage or conduit with the individual light rays of a diffuse light beam generated by the sensor shown propagating through the sensor and through a fluid shown flowing past the sensor in a tubular passage.

Accordingly, in one embodiment of the present invention, as shown in FIG. 1, a sensor 10 includes a light source 12, a layer of light diffusing material 14, a layer of transparent, light transmitting material 16 having a first refractive index, and a photosensor 18. As shown in FIG. 1, this embodiment of the sensor 10 may be fitted in the wall of a pipe 20 having a substantially circular cross-section, in which is flowing a fluid or fluid mixture 22 having a second refractive index which differs from the first refractive index and is less than the first refractive index. The sensor 10 is also coupled to a microprocessor 23 for processing the data collected from the sensor 10 to determine different properties of the fluid 22.

Preferably, the light source 12 is a laser diode, and is most preferably a 5 milliwatt He—Ne laser diode. Alternatively, a light emitting diode (LED), such as a 30 milliwatt, 2000 millicandle output LED may be used as the light source 12. Preferably, the LED is flattened to within a millimeter of the diode crystal to help bring the light source 12 closer to the layer of light transmitting material 16, and to improve the diffusion of the light beam.

The light source 12 cooperates with the layer of light diffusing material 14, such as a layer of white spray paint, for example, deposited on a first surface 24 of the light transmitting layer 16, to generate a diffuse light beam with a plurality of light rays 28. Alternatively, a source of a diffuse light beam may be used, and the light diffusing layer 14 eliminated from the sensor 10.

The light rays 28 preferably pass from the layer of light diffusing material 14 into the layer of light transmitting material 16. Preferably, the light transmitting layer 16 is fabricated from a pane of glass, most preferably normal window glass 2.731 mm (0.1075 inches) thick, although a transparent plastic material also could be used in the embodiments of the present invention. The light transmitting layer 16 may have either an arcuate cross-section to conform to the contours of the tubular pipe 20, or may have a substantially rectangular cross-section to provide a flatter surface for the attachment of the light source 12 and the photosensor 18 to the light diffusing layer 14 which is deposited on the first surface 24 of the light transmitting layer 16.

The light source 12 and the photosensor 18, preferably a photovoltaic cell or cadmium-sulfide photoresistor, are preferably attached to the light diffusing layer 14 overlying the light transmitting layer 16 using a clear adhesive, such as EPOXI-PATCH epoxy commercially available from the Dexter Corporation. The light source 12 and the photosensor 18 are preferably attached directly to the light diffusing layer 14 such that there are no gaps between the light source 12, the photosensor 18 and the light diffusing layer 14 that would affect the accuracy of the sensor 10. For example, refraction of the light beam produced by fluids, such as air, trapped in the gaps between the light diffusing layer 14 and the light source 12 or the photosensor 18 could cause a systemic error to occur in the accuracy of the sensor 10.

Figure 2:
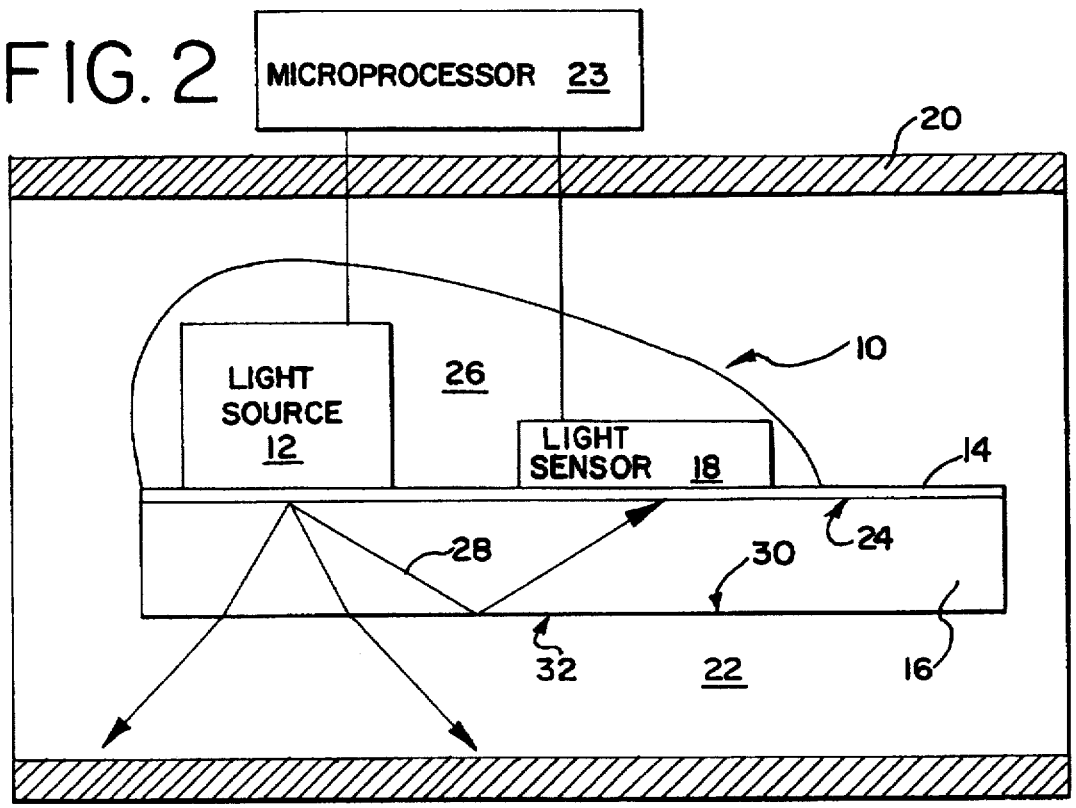
FIG. 2 is a partial cross-sectional schematic view of another embodiment of a sensor according to the present invention inserted into a passage with light rays shown propagating through the sensor and a fluid surrounding the sensor.

In an alterative embodiment of the present invention, the sensor 10 is configured to be inserted in the fluid 22, as shown in FIG. 2, by preferably applying a layer of encapsulating material 26, such as an epoxy, for example, about the light source 12 and the photosensor 18 such that the light source 12 and the photosensor 18 are encapsulated and isolated from the fluid 22. Most preferably, the epoxy is a SUPER POXEE epoxy commercially available from Watsco Components, Inc. This epoxy is specifically designed for use with refrigerants R-12, R-22, and R-502 and has been found generally suitable for use with R-134a.

In operation, the light source 12 generates or emits a focussed light beam which enters the light diffusing layer 14 on the first or upper surface 24 of the light transmitting layer 16. The light beam exits the diffusing layer 14 and enters the light transmitting layer 16 with the light beam spread out, or diffused, into a plurality of light rays 28. The light rays 28 are spaced over a wide range of angles taken relative to a normal to the first surface 24.

The light rays 28 are transmitted through the light transmitting layer 16 until the light rays 28 impinge at a second surface 30 of the light transmitting layer 16 on an interface 32 between the light transmitting layer 16 and the fluid 22. Because the index of refraction of the light transmitting layer 16, for example approximately 1.6 for glass, is greater than the index of refraction of the fluid 22, for example 1.3–1.4 for a typical mixture of oil and refrigerant, there exists a critical angle taken with respect to the normal to the interface 32, which in this embodiment is parallel to the normal to the second surface 30, at which the light rays 28 impinging on the interface 32 will not pass through the fluid 22, but will instead reflect through the light transmitting layer 16.

The plurality of light rays 28 is thus separated into two sets. The first set of light rays 28 forming an angle with the normal to the interface 32 which is greater than the critical angle is reflected back through the light transmitting layer 16. The second set of light rays 28 forming an angle with the normal to the interface 32 which is less than the critical angle is passed through the fluid 22.

Figure 3:
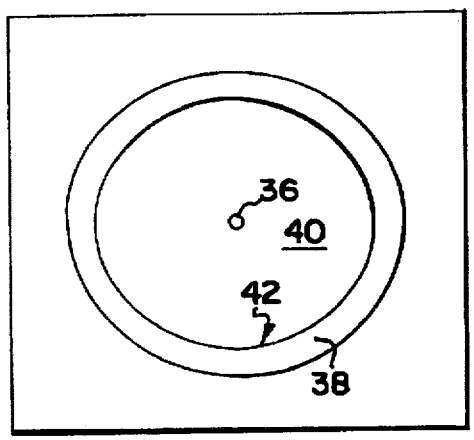
FIG. 3 is a plan view of a first or upper surface of a transparent layer or sight glass of the sensor of FIG. 1 showing the different regions of shadow and light produced during operation of the sensor.

Upon being reflected back through the light transmitting layer 16, the first set of light rays 28 impinge upon the diffusing layer 14 at a position radially removed from the position at which the diffuse light beam entered the light transmitting layer 16. Referring to FIG. 3, it can be seen that three concentric areas are formed as an incident of the light rays 28 either passing through the light transmitting layer 16 and into the fluid 22, or being reflected back through the light transmitting layer 16. An innermost area 36 of bright light is illuminated by the light beam as the light beam enters the light transmitting layer 16. An outermost area 38 of bright light is illuminated by the first set of light rays 28 being reflected back through the light transmitting layer 16. Between the brighter innermost and outermost layers 36, 38 is a darker intermediate area 40.

The relative darkness of the area 40 is caused by the second set of light rays 28 passing into the fluid 22 rather than being reflected through the light transmitting layer 16. The location of the boundary 42 light between the intermediate area 40 and the lighter, outermost area 38 can be measured using the photosensor 18, for example, or a photosensor array of which the photosensor 18 is merely a representative example. Using the data obtained from the photosensor 18 regarding the distance of the boundary 42 from the center of the diffuse beam of light rays 28, the microprocessor 23 can be used to calculate the concentration of the fluid 22, using a predetermined table correlating different indices of refraction for the fluid or fluid mixture with different concentrations of the fluid 22.

Figure 4:
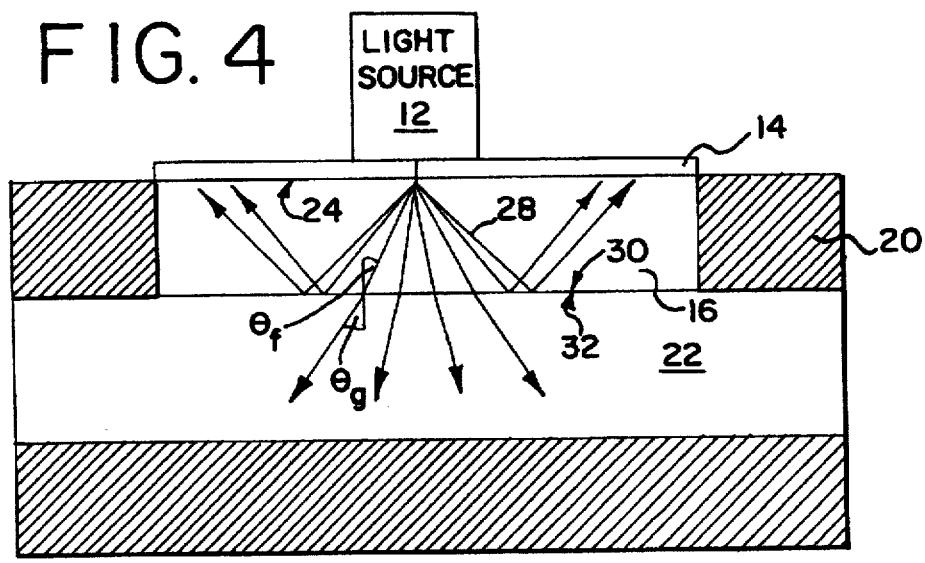
FIG. 4. is a schematic view showing the path of two sets of light rays propagating through a first and second media, the first set of light rays propagating at a first angle greater than the critical angle at the interface between the first and second media, and a second set of light rays propagating through at a second angle less than the critical angle.

Referring to FIG. 4, according to Snell's law:

$$n_f \times \sin\theta_f = n_g \times \sin\theta_g$$

where:

$n_f$=index of refraction of the fluid 22;

$n_g$=index of refraction of the light transmitting layer 16;

$\theta_f$=angle made between the light ray 28 in the fluid with respect to the normal of the second surface 30 or interface 32; and $\theta_g$=angle made between the light ray 28 in the light transmitting layer with respect to the normal of the second surface 30 or interface 32.

As explained generally above, with the refractive index of the light transmitting layer 16 greater than the refractive index of the fluid 22, there exists a critical angle, $\theta_c$, at which the light rays 28 passing through the light transmitting layer 16 will no longer pass into the fluid 22, but will reflect through the light transmitting layer 16. At the point which the light rays 28 no longer pass though the fluid 22, Snell's law reduces to:

$$n_f \times 1 = n_f = n_g \times \sin\theta_c$$

Using the sensor 10, it is possible to measure a diameter, D, of the circle defined by the boundary 42. Using basic trigonometric and geometric principles, the above equation can be rewritten as:

$$n_f = n_g \times [D^2/(16t^2 + D^2)]^{1/2}$$

where:

$n_f$=index of refraction of fluid 22;

$n_g$=index of refraction of the light transmitting layer 16;

D=diameter of the circle defined by the boundary 42; and t=thickness of the light transmitting layer 16.

Once the index of refraction for the fluid 22 is known, the index can be cross-referenced with predetermined values of the indices of refraction for different concentrations of the fluid 22. In this fashion, the concentration of the fluid 22 may be ascertained. It should be noted the primary factors influencing the sensitivity of the measurement produced using this method are the thickness of the light transmitting layer 16 and the relative difference of the refractive indices of the light transmitting layer 16 and the fluid 22.

Figure 5:
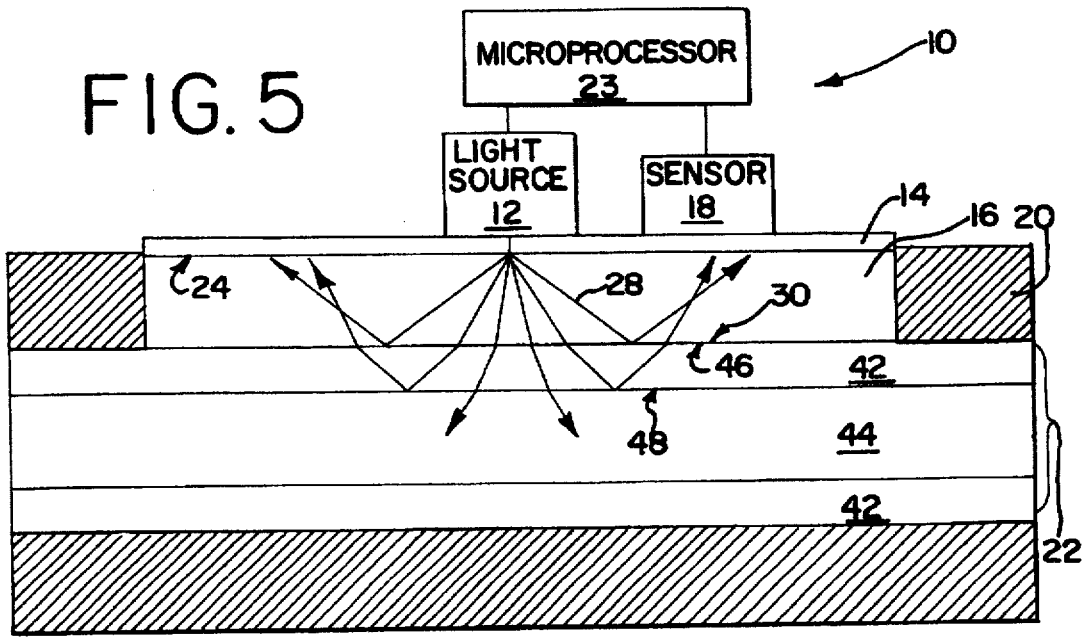
FIG. 5 is a partial cross-sectional schematic view of an embodiment of a sensor according to the present invention on a passage or conduit with individual light rays of a diffuse light beam generated by the sensor shown propagating through the sensor and a liquid phase of the two-phase fluid system shown flowing past the sensor in a tubular passage.

If the fluid 22 is not a substantially homogenous distribution of one fluid within another, but instead is made up of two or more substantially separated fluids or two or more substantially separated phases moving within the pipe 20, the sensor 10 can be used to measure properties of the two-fluid or two-phase system related to the thickness of the outermost layer of fluid or phase. For example, the embodiments of the present invention can be used to determine the thickness of a fluid film layer which is separated in a two-phase flow and is traveling along the wall of the pipe 20. Referring to FIG. 5, in which elements corresponding to the embodiment shown in FIG. 1 are similarly numbered, a light source 12 emits a light beam which impinges on a topmost surface of the light diffusing layer 14. As an incident of the light beam passing through the light diffusing layer 14, a plurality of light rays 28 are formed at various different angles to the normal of the surface 24 of the light transmitting layer 16 to which the light diffusing layer 14 is applied.

The light rays 28 travel through the light transmitting layer 16 and impinge on an interface between the light transmitting layer 16 and a two-phase fluid system having an outermost liquid film layer 42 having a preferably predetermined index of refraction less than the index of refraction of the light transmitting layer 16 and an innermost vapor core layer 44 having a preferably predetermined index of refraction less than the index of refraction of the liquid film layer 42. As an incident of the light rays 28 impinging on the interface 46 between the liquid film layer 42 and the second surface 30 of the light transmitting layer 16, a first set of light rays 28 whose angles with the normal to the second surface 30 are greater than the critical angle at the interface 46 will reflect back through the light transmitting layer 16. A second set of light rays 28 whose angles with the normal to the second surface 30 are below the critical angle at the interface 46 between the liquid film layer 42 and the light transmitting layer 16 will proceed to pass into the liquid film layer 42.

The second set of light rays 28 which pass into the liquid film layer 42 eventually reach a second interface 48 between the liquid film layer 42 and the vapor core layer 44. At the second interface 48, the second set of light rays 28 will be separated into two subsets. The first subset of light rays 28 forming an angle with the normal to the second interface 48 which is greater than the critical angle are reflected back through the liquid film layer 42, and the light transmitting layer 16, eventually impinging on the rear surface of the light diffusing layer 14. The second subset of light rays 28 forming an angle with the normal to the second interface 48 which is smaller than the critical angle will pass into the vapor core layer 44.

As a consequence, a pattern forms on the rear surface of the light diffusing layer 14 which is similar to that in FIG. 3. As shown in FIG. 6, an innermost area 50 is formed by the light rays 28 as the light rays 28 pass into the light diffusing layer 14. A darker, intermediate area 52 is formed immediately adjacent to the innermost area 50 as the light beams 28 closest to the normals of the first and second interfaces 46, 48 pass through the fluid film layer 42 and into the vapor core layer 44 without reflecting back through the light transmitting layer 16. A lighter, outermost area 54 is formed as the light rays 28 in the first set or the first subset of the second set of light rays 28 are reflected back through the light transmitting layer 16.

Provided the thickness of the sensor is substantially greater than the thickness of the fluid film layer 42, the thickness of the fluid film layer 42 may be determined by first measuring the diameter of the intermediate area 52 either mechanically using either a photosensor 18 or manually using an optical comparator with a measurement reticle. The diameter, D, or more preferably the radius, R, of the intermediate area 52 may then be used in the microprocessor 32 to find the thickness of the film layer 42 according to the following equation:

$$h_f = (R_{1,2} - R_1)/(2 \times \tan(\theta_{c2}))$$

where:

$h_f$=thickness of the fluid film layer 42;

$R_{1,2}$=radius of the intermediate area 52;

$R_1$=contribution to the radius $R_{1,2}$ from the light rays 28 as they pass through the light transmitting layer 16; and $\theta_{c2}$=critical angle at the second interface 48.

For the purposes of the equation, $R_1$ is a constant, and is calculated according to the equation:

$$R_1 = 2h_g \tan(\theta)$$

where:

$h_g$=thickness of the light transmitting layer 16; and $\theta$=angle at which the light rays 28 must strike the interface 46 to impinge upon the interface 48 at the critical angle, $\theta_c$.

$R_1$ may be found experimentally by measuring the radius of the intermediate area 52 with the pipe 20 filled with only the vapor phase.

Additionally, the response of the sensor 10 to changes in the thickness of the fluid film layer in a two-phase fluid flow can be used to calculate the velocity of a wave propagating along the interface between the liquid film layer 42 and the vapor core layer 44. Specifically, two sensors 10 of the present invention are spaced at a first distance S to each other along the pipe 20, as shown in FIG. 7, using similar numbers for elements corresponding to those shown in FIGS. 1-6. A first light source 56 and corresponding photosensor 58 are placed a first upstream location, and a second light source 60 and corresponding photosensor 62 are placed at a second downstream location.

In operation, as a wave 64 passes downstream along the second interface 48, it passes sequentially over the first light source 56 and the first photosensor 58, and then the second light source 60 and the second photosensor 62. Provided that the spacing S between the two sensors 10 is sufficiently small, the characteristics of the wave 64 change very little over the distance S between the two sensors 10. Consequently, the wave 64 induces a nearly identical response from the sensors 10 located upstream and downstream. By calculating the time delay between the responses of the first and second photosensors 58, 62, the velocity of the wave 64 can be calculated by dividing the distance between the photosensors 58, 62, S, by the time delay, $\tau$.

It should be noted, however, that the output of a photovoltaic cell is not constant due to variations in film thickness and surface angle which affect the amount of reflected light incident on the photocell. Thus, the output of the photosensors 58, 62 is not linearly proportional to the film thickness, and consequently the magnitude of the responses from the photosensors 58, 62 can not be easily determined.

The time delay between a response from the first photosensor 58 and a response from the second photosensor 62 can be found by calculating a correlation coefficient based on the cross-correlation function:

$$R_{xy}(\tau) = E[(x(t) - \mu_x)(y(t+\tau) - \mu_y)]$$

where:

x=response of the first photosensor 58;

x(t)=response of the first photosensor 58 as a function of time; p1 $\mu_x$=expected response of the first photosensor 58 as a function of time;

y=response of the second photosensor 62;

y(t)=response of the second photosensor 62 as a function of time;

$\mu_y$=expected response of the second photosensor 62 as a function of time;

E=cross-correlation function between x and y; and $\tau$=time delay of y.

When using a digital signal, Rxy is estimated by the cross-correlation estimator equation:

$$R_{xy}(\tau) = 1/(N-r) \Sigma[(x_n - \mu_x)(y_{n+r} - \mu_y)]$$

where:

r=number of data points by which y is shifted back in time; and

N=total number of data points.

Dividing the estimator equation by the standard deviation of the responses, x and y, yields the correlation coefficient, $\rho_{xy}$. The time at which the correlation coefficient reaches a maximum is the time delay between the signals x and y. The distance S between the sensors 10 can then be divided by this time delay to determine the velocity of the wave 64.

Still other aspects, objects, and advantages of the present invention can be obtained from a study of the specification, the drawings, and the appended claims.

We claim:

1. A sensor system comprising:

a first layer having first and second sides and a first index of refraction;

a second layer disposed to one of the first and second sides of the first layer and having a second index of refraction which is less than the first index of refraction;

means for generating a first diffuse light beam which is initially directed along a first line through the first layer in a first direction; and means for sensing the location relative to the first line of a portion of the first diffuse light beam reflected back through the first layer as an incident of the first diffuse light beam impinging upon the second layer.

2. The sensor system according to claim 1, wherein the second layer is disposed on the first layer so as to define an interface between the first and second layers, the portion of the first diffuse light beam reflected through the first layer as an incident of the first diffuse light beam impinging the interface.

3. The sensor system according to claim 1, further comprising:

a third layer disposed between the first layer and the second layer having a thickness and a third index of refraction which is less than the first index of refraction and greater than the second index of refraction.

4. The sensor system according to claim 3, wherein the second layer is disposed on the third layer so as to define an interface between the second and third layers, the portion of the first diffuse light beam reflected through the first layer as an incident of the first diffuse light beam impinging the interface.

5. The sensor system according to claim 4 in combination with:

means for generating a second diffuse light beam which is initially directed along a second line through the first layer in a second direction, the second diffuse light beam generating means disposed a predetermined distance from the first diffuse light beam generating means;

means for sensing the location relative to the second line of a portion of the second diffuse light beam reflected back through the first layer as an incident of the second diffuse light beam impinging the interface defined between the second and third layers; and means coupled to the first and second diffuse light beam sensing means for determining the velocity of a localized disturbance in the thickness of the third layer as a function of the time elapsed between the first and second diffuse light beam sensing means sensing the portions of the first and second light beams reflected through the first layer as an incident of the change in thickness of the third medium caused by the localized disturbance.

6. A sensor system comprising:

a first layer having first and second surfaces and a first index of refraction;

a second layer having a second index of refraction which is less than the first index of refraction;

means for generating a first diffuse light beam which is initially directed along a first line through the first layer from the first surface to the second surface in a first direction;

means for sensing a portion of the first diffuse light beam reflected back through the first layer to the first surface as an incident of the first diffuse light beam impinging upon the second layer, the second layer being disposed on the first layer so as to define an interface between the first and second layers, the portion of the first diffuse light beam reflected through the first layer to the first surface as an incident of the first diffuse light beam impinging the interface; and means coupled to the sensing means for determining the index of refraction of the second layer as a function of the distance along the first surface between the first line and the reflected portion of the first diffuse beam.

7. A method of determining the properties of a medium, the method comprising the steps of:

generating a first diffuse light beam;

passing the first diffuse light beam through a first medium having a first index of refraction;

causing a portion of the first diffuse light beam to be initially directed along a first line through the first medium in a first direction, to impinge upon a second medium having a second index of refraction less than the first index of refraction and to reflect back into the first medium; and sensing the location relative to the first line of the portion of the first diffuse light beam reflected back into the first medium.

8. The method of claim 7, the causing step further comprising causing the portion of the first diffuse light beam to impinge an interface defined between the first and second media and reflect back into the first medium.

9. The method of claim 7, the causing step further comprising:

causing the portion of the first diffuse light beam to pass through a third medium having a thickness and a third index of refraction which is less than the first index of refraction and greater than the second index of refraction, the third medium disposed between the first and second media; and causing the portion of the first diffuse light beam to impinge an interface defined between the second and third media and to reflect back into the first medium.

10. The method according to claim 9, further comprising:

sensing a portion of the first diffuse light beam reflected back into the first medium as an incident of a disturbance moving along the interface between the second and third media;

generating a second diffuse light beam;

passing the second diffuse light beam through the first medium initially along a second line in a second direction at a predetermined distance from the first diffuse light beam;

sensing the location relative to the second line of a portion of the second diffuse light beam reflected back into the first medium as an incident of the disturbance moving along the interface between the second and third media;

measuring the time elapsed between the step of sensing of the portion of the first diffuse light beam reflected back as an incident of the disturbance moving along the interface between the second and third media and the step of sensing the portion of the second diffuse light beam reflected back as an incident of the disturbance moving along the interface between the second and third media; and determining the velocity of the disturbance moving along the interface between the second and third media as a function of the time elapsed between the step of sensing the portion of the first diffuse light beam reflected back into the first medium as an incident of the disturbance moving along the interface between the second and third media, and the step of sensing the portion of the second diffuse light beam reflected back into the first medium as an incident of the disturbance moving along the interface between the second and third media.

11. A method of determining the properties of a medium, the method comprising the steps of:

generating a first diffuse light beam;

passing the first diffuse light beam through a first surface of a first medium having a first index of refraction;

causing a portion of the first diffuse light beam to be initially directed along a first line through the first medium, to impinge upon a second medium having a second index of refraction less than the first index of refraction and to reflect back to the first surface, the causing step further comprising causing the portion of the first diffuse light beam to impinge an interface defined between the first and second media and reflect back to the first surface;

sensing the portion of the first diffuse light beam reflected back to the first surface;

measuring the distance along the first surface between the first line and the portion of the first diffuse light beam reflected back to the first surface; and determining the index of refraction of the second medium as a function of the distance along the first surface between the first diffuse light beam and the portion of the first diffuse light beam reflected back to the first surface.

12. A sensor system comprising:

a first layer having first and second surfaces and a first index of refraction;

a second layer having a second index of refraction which is less than the first index of refraction;

a third layer disposed between the first layer and the second layer having a thickness and a third index of refraction which is less than the first index of refraction and greater than the second index of refraction, the second layer being disposed on the third layer so as to define an interface between the second and third layers;

means for generating a first diffuse light beam which is initially directed along a first line through the first layer in a first direction from the first surface to the second surface;

means for sensing a portion of the first diffuse light beam reflected back through the first layer to the first surface as an incident of the first diffuse light beam impinging upon the interface; and means coupled to the sensing means for determining the thickness of the third layer as a function of the distance along the first surface between the first line and the reflected portion of the first diffuse beam.

13. A method of determining the properties of a medium, the method comprising the steps of:

generating a first diffuse light beam;

passing the first diffuse light beam through a first surface of a first medium having a first index of refraction;

causing a portion of the first diffuse light beam to be initially directed along a first line through the first medium in a first direction, to impinge upon a second medium having a second index of refraction less than the first index of refraction and to reflect back to the first surface including causing the portion of the first diffuse light beam to pass through a third medium having a thickness and a third index of refraction which is less than the first index of refraction and greater than the second index of refraction, the third medium disposed between the first and second media, and causing the portion of the first diffuse light beam to impinge an interface defined between the second and third media and to reflect back to the first surface;

sensing the portion of the first diffuse light beam reflected back to the first surface;

measuring the distance along the first surface between the first line and the portion of the first diffuse light beam reflected back to the first surface; and calculating the thickness of the third medium as a function of the distance along the first surface between the first direction of the diffuse light beam and the portion of the first diffuse light beam reflected back to the first surface.

* * * * *